US006790456B2

(12) United States Patent
Vogel et al.

(10) Patent No.: US 6,790,456 B2
(45) Date of Patent: Sep. 14, 2004

(54) INJECTABLE AND SWELLABLE MICROSPHERES FOR DERMAL AUGMENTATION

(75) Inventors: Jean-Marie Vogel, Boxborough, MA (US); Egisto Boschetti, Gougenot (FR)

(73) Assignee: Biosphere Medical, Inc., Rockland, MA (US)

( * ) Notice: Subject to any disclaimer, the term of this patent is extended or adjusted under 35 U.S.C. 154(b) by 170 days.

(21) Appl. No.: 10/222,819

(22) Filed: Aug. 19, 2002

(65) Prior Publication Data

US 2002/0197326 A1 Dec. 26, 2002

Related U.S. Application Data

(63) Continuation of application No. 09/528,990, filed on Mar. 20, 2000, now Pat. No. 6,436,424.

(51) Int. Cl.[7] .......................... A61F 13/00; A61F 2/00; A61K 9/16; A61K 9/50
(52) U.S. Cl. ...................... 424/423; 424/400; 424/423; 424/489; 424/501
(58) Field of Search ............................ 424/400, 422, 424/423, 489, 501

(56) References Cited

U.S. PATENT DOCUMENTS

| | | | |
|---|---|---|---|
| 3,919,411 A | 11/1975 | Glass et al. | 424/81 |
| 4,197,846 A | 4/1980 | Bucalo | 128/218 |
| 4,413,070 A | 11/1983 | Rembaum | 523/223 |
| 4,452,916 A | 6/1984 | Boschetti | 521/38 |
| 4,500,658 A | 2/1985 | Fox | 523/117 |
| 4,525,358 A | 6/1985 | Baltes et al. | 514/255 |
| 4,622,362 A | 11/1986 | Rembaum | 525/54.1 |
| 4,786,555 A | 11/1988 | Howard, Jr. | 428/403 |
| 4,803,075 A | 2/1989 | Wallace et al. | 424/423 |
| 5,007,940 A | 4/1991 | Berg | 514/225 |
| 5,306,500 A * | 4/1994 | Rhee et al. | 424/422 |
| 5,324,775 A * | 6/1994 | Rhee et al. | 525/54.2 |
| 5,344,452 A | 9/1994 | Lemperle | 623/11 |
| 5,451,406 A * | 9/1995 | Lawin et al. | 424/423 |
| 5,470,911 A | 11/1995 | Rhee et al. | 525/54.1 |
| 5,550,188 A | 8/1996 | Rhee et al. | 525/54.1 |
| 5,578,709 A | 11/1996 | Woiszwillo | 530/410 |
| 5,633,001 A | 5/1997 | .ANG.gerup | 424/423 |
| 5,635,215 A | 6/1997 | Boschetti et al. | 424/501 |
| 5,648,100 A | 7/1997 | Boschetti et al. | 424/501 |
| 5,922,025 A * | 7/1999 | Hubbard | 424/423 |
| 6,335,028 B1 | 1/2002 | Vogel et al. | 424/422 |

FOREIGN PATENT DOCUMENTS

| | | |
|---|---|---|
| EP | 0 648 480 A2 | 4/1995 |
| EP | 0648480 A2 * | 4/1995 |
| EP | 0 713 707 A1 | 5/1996 |
| EP | 0 811 373 A2 | 12/1997 |
| FR | 2378808 | 8/1978 |
| JP | 6056676 | 3/1994 |
| WO | WO 92/21327 | 12/1992 |
| WO | WO 9221327 A1 * | 12/1992 | A61K/9/16 |
| WO | WO 99/31167 | 6/1999 |
| WO | WO 99/44643 | 9/1999 |

OTHER PUBLICATIONS

Eppley et al. "A Potential Biomaterial Composite for Dermal and Subcutaneous Augmentation", Annals of Plastic Surgery, 32 (5): 463–468 (1994).*

Boschetti E., Microspheres for Biochromatography and Biomedical Applications; Part I, Preparation of Microbeads In:Microspheres, Microencapsulation and Liposomes, John Wiley & Sons, Arshady R., Ed. 2: 171–189 (1999).

Boschetti E., "Polyacrylamide Dericatives To The Service of Bioseparations,"*J. Biochem–Biophys. Meth.*, 19:21–36 (1989).

Boschetti E. et al., "Synthese et copolymerisation de nouveaux monomeres acryliques diiodes et triiodes,"*Bull. Soc. Chim.Fr.*. 4:669–677 (1996).

Brown et al., "Syntheses and copolymerizations of new water–soluble polyiodinated acrylic monomers," *Makromol. Chem. Rapid Commun.* 6: 503–507 (1985).

Cherksey B.D. et al., "Adrenal Chromaffin Cells on Microcarriers Exhibits Enhanced Long–Term Functional Effects When Implanted into the Mammalian Brain," *IBRO*, 657–664 (1996).

Chowdhury R. et al., In: Advanced Research on Animal Cell Technology, A.O.A. Miller ed., Kluwers Acad. Press, 315–327(1989).

Edgerton et al., "Indications for and pitfalls of soft tissue augmentation with liquid silicone," Plast. Reconstr. Surg., 58:157–163 (1976).

Eppley B. L. et al., "A Potential Biomaterial Composite for Dermal and Subcutaneous Augmentation," *Annals of Plastic Surgery*, 32(5):463–468 (1994).

Krukowski, et al. "Charged Beads Stimulate Bone Formation" 34th Annual Meeting Orth. Res. Soc. Feb. 1988.

Laurent A. et al., "Trisacryl Gelatin Microsphere For Therpeutic Embolization, I: Development and In Vitro Evaluation," *Am. J. Neuroradiol.*, 17:533–540 (1996).

Laurent A. et al., "Trisacryl Gelatin Microsphere For Therpeutic Embolixation, I: Development and In Vitro Evaluation," *Am. J. Neuroradiol.*, 17:533–540 (1996).

(List continued on next page.)

Primary Examiner—Thurman K. Page
Assistant Examiner—S. Tran
(74) *Attorney, Agent, or Firm*—Jones Day

(57) ABSTRACT

The present invention relates to injectable compositions comprising biocompatible, swellable, hydrophilic, non-toxic and substantially spherical microspheres microspheres and a biocompatible carrier for use in dermal augmentation. The present invention further relates to methods of dermal augmentation, particularly for the treatment of skin contour deficiencies, using the injectable compositions.

44 Claims, No Drawings

OTHER PUBLICATIONS

Levine D.W. et al., "Microcarrier Cell Culture: New Methods for Research–Scale Application," *Somatic Cell Genetics*, 3:149–155 (1977).

Mazza et al., "Polymer Design in Dye Chromatography: From the definition of monomers to the evaluation of polymeric supports, " in Protein–Dye Interactions: Developments and Applications, Vijayalakshmi M.A. ed., Elsevier Appl. Sciences, Elsevier Sci. Publ. Ltd., pp. 126–136 (1989).

Millikan, "Long Term Safety and Efficiency with Fibrel in the Treatment of Cutaneous Scars", J Dermatol Surg Oncol, 15:837–846 (1989).

Obrenovitch A. et al., "Microcarrier Culture Of Fibroblastic Cells On Modified Trisacryl Beads," *Biol. Cell.*, 46:249–256 (1983).

Remacle, C. et al., "Cultures of Preadipocytes on Microparticles Their Properties of Adhesion Proliferation and Differentation," *Manuscript from Univeristy of Catholique de Louvain, Laboratiore de Biologie Cellulaire*, 1–33.

Van Wezel, A.L., "Growth of Cell–strains And Primary Cells On Micro–carries In Homogeneous Culture," *Nature*, 216:64–65 (1967).

* cited by examiner

INJECTABLE AND SWELLABLE MICROSPHERES FOR DERMAL AUGMENTATION

This is a continuation of application Ser. No. 09/528,990, filed Mar. 20, 2000, now U.S. Pat. No. 6,436,424.

1. FIELD OF INVENTION

The present invention relates to dermal augmentation, particularly for the treatment of skin contour deficiencies, using injectable compositions comprising swellable hydrophilic microspheres.

2. BACKGROUND OF THE INVENTION

Damage to the skin due to aging, environmental exposure to the sun and other elements, weight loss, child bearing, disease such as acne and cancer, and surgery often results in skin contour deficiencies and other skin anomalies. In order to correct contour deficiencies and other anomalies of the skin, people often resort to cosmetic surgery, such as face lifts and skin tucks. Cosmetic surgery, however, has several drawbacks, in addition to the high cost associated with it. It is usually an invasive and risky procedure, having the potential of leaving scars in areas of operation and affecting normal biological and physiological functions. Furthermore, cosmetic surgery is often a limited option, available only for certain skin deficiencies.

In addition to cosmetic surgery, various other methods are used to remove or ameliorate the deficiencies with different levels of success. The use of injectable material for soft tissue augmentation is a method often used. The advantage of using hypodermic needles as a delivery device for dermal augmentation reflects the advantages of using hypodermic needles in general: easy, precise and, usually, non-invasive deliveries. Yet, the requirement for such use is also quite strict: the material to be delivered must be deliverable through the needles, which means the material must be able to easily pass through the hollow centers of the needles.

One method of dermal augmentation using injectable material is liquid or semi-liquid injections, usually containing collagen. The best known example is a collagen preparation manufactured by Collagen Corporation (now part of Inamed Corporation) and marketed by C. R. Bard. However, collagen is a naturally occurring substance which the body may enzymatically degrade and eliminate over time, thus requiring repeat treatments. Also, collagen may be displaced within the tissue in which it was originally injected, thereby reducing or eliminating the intended dermal augmentation effect. Collagen is also digested directly (biochemically), through macrophages, through the lymphatic system, or by other means. Even more alarming from a cosmetic perspective, collagen may move from the initial site of injection, causing unsightly bumps and bulges under the skin at undesired locations. See, e.g., Millikan, Long Term Safety and Efficacy with Fibrel in the Treatment of Cutaneous Scars, *J Dermatol Surg Oncol,* 15:837–846 (1989).

Injection of liquid silicone has also been used extensively. However, due to long term side effects, such as nodules, recurring cellulitis, and skin ulcers, the use of injectable silicone is on the decline. See, e.g., Edgerton et al., Indications for and pitfalls of soft tissue augmentation with liquid silicone, *Plast. Reconstr. Surg,* 58:157–163 (1976).

Solid microparticles have also been used for the correction of skin deficiencies. For example, carbon particles, silicone particles, TEFLON paste, collagen beads and polymethylmethacrylate spheres, have been used with disappointing results due to, inter alia, adverse tissue reactions, biological degradation and migration from the initial implantation location. U.S. Pat. No. 5,451,406 discloses an injectable biocompatible composition for tissue augmentation comprising a plurality of discrete substrate particles with a carbon coating in a carrier. The substrate particles in the '406 patent are metallic substrate such as stainless steel, titanium, titanium alloy, and their oxides.

The problems associated with rigid and non-deformable particles, such as metal particles, carbon particles and silicone particles, in treating skin deficiencies are that they are either too fragile or too large to be injected, or too small and are digested or eliminated by the body. Therefore, such particles all have one or more of the following limitations: (i) too large to be injected through a 30 gauge or smaller needle; (ii) particles of irregular shape clump together, making injection difficult; (iii) particles are too fragile, resulting in breakage during injection and digestion of the residues; (iv) injected particles are too small and are digested by macrophages or other components of the lymphatic system; and (v) injected particles are displaced as they do not adhere to the surrounding cells.

Injectable deformable particles, such as TEFLON particles, have also been used for tissue augmentation, but results are also unsatisfactory. Such particles do not stay at the site of injection as they are deformed during and after injection, resulting in sliding within the tissue. They also do not return to their original shape, resulting in digestion by the body because their diameters become smaller during the injection process. For example, U.S. Pat. No. 5,007,940 discloses injecting deformable nonbiodegradable hydrogels with a lubricious surface into the brain tissues. Because of the nature of the hydrogels, the material injected has a risk of sliding of being carried away by the venous blood to central parts of the body, resulting in both less effective tissue augmentation and adverse effects to the body.

U.S. Pat. No. 5,633,001 discloses a biocompatible composition for tissue augmentation comprising a pseudoplastic polymer carrier (e.g., glucose amine glucans, hydroxy ethyl cellulose, carboxy methyl cellulose, xanthan gum, and alginates) and a water insoluble, biocompatible and biodegradable tissue augmenting substance comprising a dextranomer.

It is clear that there is still a great need for a safe, biocompatible, stable and effective method of dermal augmentation for the treatment of skin deficiencies. There is also a need for stable and biocompatible injectable compositions for dermal augmentation.

3. SUMMARY OF THE INVENTION

The present invention provides injectable compositions comprising swellable microspheres and method of using the injectable compositions to perform dermal augmentation, particularly for treatment of skin contour deficiencies, in a mammal. The composition is injectable through 30 gauge or smaller needles and the microspheres are not capable of being eliminated by macrophage (digested) or other elements of said mammal's immune system after injection.

The microspheres of the present invention are highly water absorbing and capable of swelling to many times of their original sizes under certain conditions. The microspheres of the present invention generally comprise crosslinked polymers. Preferably, the microspheres comprise sodium acrylate polymer, acrylamide polymer, acrylamide derivative polymer or copolymer, sodium acrylate and vinyl alcohol copolymer, vinyl acetate and acrylic acid ester copolymer, vinyl acetate and methyl maleate copolymer, isobutylene-maleic anhydride crosslinked copolymer, starch-acrylonitrile graft copolymer, crosslinked sodium polyacrylate polymer, crosslinked polyethylene oxide, or mixtures thereof. These microspheres are capable of swelling upon contacting with medium resembling the properties of physiological fluids, thus allowing the microspheres to secure themselves into position after injection into the body. Furthermore, the microspheres are substantially spherical and can be easily calibrated so that their sizes can be accurately determined. The microspheres of the invention have diameters from about 10 to about 400 $\mu$m before swelling. Preferably, before swelling, the diameters of the microspheres are from about 10 to about 200 $\mu$m and, most preferably, from about 10 to about 120 $\mu$m. After injection and swelling, the microspheres have average diameters larger than about 40 $\mu$m, preferably larger than about 50 $\mu$m and, more preferably, larger than about 70 $\mu$m.

In a preferred embodiment of the present invention, the microspheres further comprise cell adhesion promoters or cells on at least a portion of their surfaces. The cells are preferably autologous cells from the subject mammal. Most preferably, the cells are autologous cells from the same type of tissues being treated, such as fat cells, muscle cells, subcutaneous cells, dermal cells, and epidermal cells.

The microspheres of the present invention may further comprise a therapeutic or prophylactic agent, radiopacifying agent, contrast agent or other detectable substances, targeting agent, or mixtures thereof, providing therapeutic and other benefits to the skin in addition to dermal augmentation.

In a preferred embodiment, the composition of the present invention comprises the microspheres in an amount ranges from about 10% to about 90% by weight and the biocompatible carrier from about 10% to about 90% by weight. Preferably, the injectable composition is a suspension of the microspheres in the biocompatible carrier. The biocompatible carrier of the present invention is preferably a solvent in which the microspheres are suspended. The solvent is preferably in such a condition that the microspheres can be uniformly suspended and, more importantly, that the swelling of the microspheres are also controlled by adjusting the solvent, the salt and ionic concentration, the pH value, or combinations thereof. Suitable solvents for the present invention include aqueous based solutions such as saline solutions, PBS solutions, alcohol based solutions, and other biocompatible hydro-organic solutions known in the art.

The microspheres of the present invention are capable of swelling upon contact with physiological fluids, including blood, and cells and tissues at the injection site. The degree of swelling depends on factors such as the material of the microspheres and the degree of crosslinking, the solvent in which the microspheres were suspended before injection, and the biological and physiological conditions at the site of injection. Therefore, knowing the site of injection and its biological and physiological conditions will allow control of the degree of swelling of the microspheres after injection by selecting the material for microspheres and the solvent in which they are suspended.

In a preferred embodiment, there is no aggregation or clumping of the microspheres in the injectable composition before and during injection. The injectable composition of the invention further comprises a cell adhesion promoter, cells or both associated with the microspheres, including on the surface of the microspheres. In addition, the injectable composition can contain one or more of a therapeutic or prophylactic agent, radiopacifying agent, and contrast agent or medium or other detectable substances to provide therapeutic and other benefits while performing dermal augmentation.

The present invention additionally provides methods of dermal augmentation and treatment of skin deficiency. Specifically, the invention provides a method of causing dermal augmentation in a mammal by administering a composition of swellable, hydrophilic, substantially and non-toxic spherical microspheres in a biocompatible carrier to the mammal. The composition is injectable through a needle of about 30 gauge or smaller and the microspheres are not capable of being digested or eliminated by macrophage or other elements of the mammal's immune system. According to the present invention, a preferred method of administration is injecting the composition into an area of the subject mammal that is in need of dermal augmentation. A more preferred method of administration is injecting the composition into the subcutaneous layer of the subject mammal at the treatment site.

The dermal augmentation method of the present invention is especially suitable for the treatment of skin contour deficiencies, which are often caused by aging, environmental exposure, weight loss, child bearing, injury, surgery, in addition to diseases such as acne and cancer. Suitable for the treatment by the present invention's method are contour deficiencies such as frown lines, worry lines, wrinkles, crow's feet, marionette lines, stretch marks, and internal and external scars resulted from injury, wound, bite, surgery, or accident.

The invention also encompasses the use of the injectable compositions to treat skin deficiencies caused by diseases such as acne and cancer. Further, the invention encompasses the treatment of scars on or within the skin caused by accidents, wounds and injuries.

The present invention further provides a method of causing dermal augmentation by administering the injectable suspension extracorporeally into organs, components of organs, or tissues prior to their inclusion into said mammal's body, organs, or components of organs.

The present invention additionally provides a kit for performing dermal augmentation. The dermal augmentation kit of the present invention comprises a 30 gauge or smaller needle and a corresponding syringe, wherein the syringe contains a composition comprising biocompatible, swellable, hydrophilic, non-toxic and substantially spherical microspheres and a biocompatible carrier. The composition is injectable through the needle and the microspheres are not capable of being digested or eliminated by macrophage or other elements of said mammal's immune system. Alternatively, the syringe does not contain a solution or suspension but is accompanied by (a) dry microspheres which are ready for preparation of a suspension; (b) a preformed suspension of microspheres; and (c) dry microspheres and a biocompatible solution in separate containers.

4. DETAILED DESCRIPTION OF THE INVENTION

The present invention provides a safe, effective, stable, and long lasting method for treating skin deficiencies by using novel injectable compositions comprising swellable microspheres for dermal augmentation. The present invention encompasses injectable compositions comprising swellable, hydrophilic, non-toxic, and, preferably, substantially spherical microspheres useful for dermal augmentation. The invention also provides methods of dermal augmentation and treating skin deficiencies by administrating the injectable composition to a mammal in need of treatment. The microspheres, injectable compositions, and methods of dermal augmentation of the present invention encompass the following advantages: (1) the injected materials are not easily displaced within the tissues in which they were originally injected, (2) the injected materials are not readily eliminated either biochemically or through macrophage or other elements of the immune system, (3) the materials are of sufficient size to be injected through 30 gauge or smaller needles, (4) the injected particles are flexible and not fragile, facilitating easy injection without being broken, and, preferably, and, preferably, (5) the injected particles are not irregularly shaped and do not clump together. These benefits, whether alone or in combinations, enhance the effectiveness of the treatment and are safe, more convenient and comfortable for patients.

As used in the present invention, "microspheres" means polymer or combinations of polymers made into bodies of various sizes. The microspheres can be in any shape, although they are often in substantially spherical shape. Preferably, the microspheres contained in the injectable compositions of the present invention are sterile.

"Swellable" microspheres, as used in the present invention, refers to microspheres that are capable of being enlarged in size, yet still retain substantially the same shape, upon certain conditions such as contacting physiological fluids. Preferably, the swellable microspheres of the present invention can be enlarged to about 4 times of their original diameter or 15 times of their original volume. The degree of swelling can be controlled by controlling factors such as the solvents in which they are suspended, specific polymers used to make the microspheres and degree of crosslinking. This property enables the microspheres be easily injected through needles of 30 gauge or smaller, yet be enlarged and secured at the injection site and of sufficient size to avoid or reduce the chance of being eliminated by the immune system of the mammal.

"High water absorbing polymers" as used in the present invention refers to polymers that can absorb at least 5% water by weight or that are capable of increasing the dry weight of the polymers to about 20 times of their original dry weight.

The microspheres of the present invention also comprise particles that are "hydrophilic," which, as used in the invention, means the particles can dissolve in, absorb, or mix easily with water or aqueous solution.

"Biodegradable" microspheres refer to microspheres that are capable of being absorbed by the body, chemically, physiologically, or by other biological means, over a period of time.

"Substantially spherical" generally means a shape that is close to a perfect sphere, which is defined as a volume that presents the lowest external surface area. Specifically, "substantially spherical" in the present invention means, when viewing any cross-section of the particle, the difference between the average major diameter and the average minor diameter is less than 20%. The surfaces of the microspheres of the present invention appear smooth under magnification of up to 1000 times. The microspheres of the present invention may comprise, in addition to the particles, other materials as described and defined herein.

"Dermal augmentation" in the context of the present invention refers to any change of the natural state of a mammal's skin and related areas due to external acts. The areas that may be changed by dermal augmentation include, but not limited to, epidermis, dermis, subcutaneous layer, fat, arrector pill muscle, hair shaft, sweat pore, and sebaceous gland.

"Cell adhesion promoter" in the present invention means any material that, because of their presence in or association with the microspheres, promotes or enhances the adhesiveness of cells to the surface of the microspheres. These materials are often proteins that are bound to the surface of the microspheres through covalent bonds of the proteins and the polymers.

"Therapeutic agent" in the present invention refers to any substance that provides therapeutic effects to the process of dermal augmentation or biological or physiological responses to the dermal augmentation. An example of therapeutic agent is an anti-inflammation agent that prevents or reduce the effect of inflammations associated dermal augmentation, an anti-bacterial, anti-fungal, or anti-histamine agent.

"Chemical modification" in the present invention means the changes of chemical properties and characteristics of the microspheres, either during their production process or by way of mixing or contacting them with various agents or tissues, such that the microspheres have the ability to perform, in addition to dermal augmentation, other functions once injected into the body.

For clarity of disclosure, and not by way of limitation, the detailed description of the present invention is divided into the subsections which follow.

4.1. Microspheres

Microspheres for use in the present invention are based on non-toxic, biocompatible, swellable, hydrophilic, and substantially spherical particles which comprise various polymers. The microspheres of the present invention comprise crosslinked polymers that are high water absorbing and, thus, capable of swelling upon contacting with aqueous medium in certain conditions. As understood by a person skilled in the art, the degree of swelling of crosslinked polymers generally depends on the properties of the polymeric materials such as their ionic character, the hydrophilicity of the polymeric materials, and the degree of crosslinking. Properties, such as salt and ionic concentration and level of pH, of the solvent in which the microspheres are suspended or with which the microspheres are contacting also affect the degree of swelling.

As disclosed herein, by controlling the size and the degree of swelling of certain crosslinked and swellable polymers, safe, effective, and long lasting dermal augmentation can be achieved using these microspheres. According to the invention, polymeric materials having high water absorbing ability are first chosen. The swellability of these polymers can be further manipulated by controlling the polymer's ionic character and the degree of crosslinking by methods known to a skilled artisan.

The microspheres of the present invention can be either anionic or cationic. Preferably, cationic microspheres are used because of their superior ability of promoting cell adhesion. The crosslinking degree of the microspheres can be changed either chemically or through radiation. A variety of crosslinking agents may be used, including, but not limited to, tetraethylene glycol diacrylate, tetraethylene glycol dimethacrylate, ethylene glycol dimethacrylate, methacrylate, and pentaerythritol dimethacrylate. The microspheres of the invention may comprise from about 0.5% to about 20%, by molecular weight, of crosslinkers. Preferably, the microspheres comprise from about 1% to about 5%, by molecular weight, of crosslinkers.

More importantly, the present invention has discovered that the swelling of the microspheres comprising these polymers can be further controlled by controlling the solvent in which the microspheres are suspended. This is achieved through two steps as disclosed herein. First, the size of the microspheres before injection are controlled by using appropriate solvents, salt concentration and pH level according to the specific microspheres used. The microspheres before injection may either remain in their original size or swell to certain degree due to their contact with the solvent. The pre-injection swelling is controlled so that the microspheres are easily injectable through 30 gauge or smaller needles. Second, after injection and upon contacting with tissues at injection site, the microspheres may further swell into predetermined size or retain their pre-injection size, either of which size will allow the microspheres to be secured at the site of injection and achieve desired dermal augmentation effect. The degree of pre-injection swelling, and thus the after injection swelling, is determined by the particular microspheres used and the nature and location of the skin deficiencies being treated.

Microspheres for use in the present invention have diameters range from about 10 to about 400 $\mu$m before swelling. Preferably, before swelling, the diameters of the microspheres are from about 10 to about 200 $\mu$m and, most preferably, from about 10 to about 120 $\mu$m. After injection and swelling, the microspheres have average diameters larger than about 40 $\mu$m, preferably larger than about 50 $\mu$m and, more preferably, larger than about 70 $\mu$m. The microspheres of the present invention are capable of swelling to about 4 times of their original diameters or about 15 times of their original volume. The full swollen size of the microspheres after injection are controlled, by various means discussed above, so that they are secured at the site of injection while not causing any potential injuries to the tissues. Further, the full swollen sizes of the microspheres after injection are predetermined based on factors such as the physiological conditions of the injection site, the original microspheres sizes, the solvent used and the pre-injection swelling of the microspheres. Thus, a specific injection plan can be designed according to the particular dermal augmentation need of the case. These sizes and properties of the microspheres are advantageous in that they enable the microspheres to be easily injectable through needles of 30 gauge or smaller, yet the microspheres are large enough so that they will be secured at the site of injection and will not be digested or eliminated by macrophage or other elements of the immune system.

The microspheres are also resistant to injection force created by 30 gauge or smaller needles and to the muscle contraction stress generated during and after the injection process. The microspheres are also thermally stable which allows for easy, convenient sterilization, and frozen storage for the preparation of injection.

Many types of crosslinked polymers having high water absorbing ability are suitable for use in the present invention as long as they are non-toxic to tissues and cells and are biocompatible. Preferably, the polymers are selected from the group consisting of sodium acrylate polymer, acrylamide polymers, acrylamide derivative polymers or copolymers, sodium acrylate and vinyl alcohol copolymer, saponification products of copolymer of vinyl acetate and acrylic acid ester, vinyl acetate and acrylic acid ester copolymer, vinyl acetate and methyl maleate copolymer, isobutylene-maleic anhydride crosslinked copolymer, starch-acrylonitrile graft copolymer and its saponification products, crosslinked sodium polyacrylate polymer, and crosslinked polyethylene oxide.

The microspheres of the present invention can be biodegradable or non-biodegradable. The microspheres are always sterilized before being composed into a suspension for injection. Further, the microspheres of the present invention are thermally stable which allows for easy, convenient sterilization, and frozen storage. The microspheres for use in the present invention are also stable in suspension which allows the microparticles to be formulated and stored in suspension and injected with different liquids or oils. More specifically, the hydrophilic nature of the microspheres permits placing them in suspension, and in particular, in sterile form of injectable solutions, while avoiding the formation of aggregates or adhesion to the walls of storage containers and implantation devices, such as catheters, syringes, needles, and the like.

The microspheres of the present invention may contain within their structure or on their surfaces other chemicals, therefore displaying particular properties, such as therapeutic, radio-pacifying, and contrasting effects; promotion of cell adhesion; and capability of being chemically modified.

The microspheres of the present invention may further associated with contrast medium or agent. Contrast media useful within the present invention can be found in Dawson et al. *Contrast Medium in Practice* (Springer-Verlag, 1994). Contrast media include, but not limited to, ultrasonic media, superparamagnetic media, and gadolinium contrast media. Preferably, the contrast media are any media that contain barium or iodine salts, such as high molecular weight salts, including acylamino-e-propion-amido-3-triiodo-2,4,6-benzoic acid, which can be prepared under the conditions described by Boschetti et al. (*Bull. Soc. Chim.*, No. 4 France, (1986)). In the case of barium or magnetite salts, they can be directly introduced in powered form in the initial monomer solution.

In another embodiment of the invention, the microspheres have specific properties suitable for cell adhesion and cells growth promotion, making the microspheres particularly useful for certain dermal augmentation. Cells are associated with the microspheres, through adhesion or other means, prior to injection. Preferably, the cells are autologous cells from the subject mammal. These autologous cells are preferably the same type of cells that need to be repaired in the dermal augmentation, such as fat cells, muscle cells, subcutaneous cells, dermal cells, epidermal cells, or combinations thereof. The autologous cells may also preferably be cells that enhance or promote the growth or connection of cells or tissues, such as fibroblast.

Various types of cell adhesion promoters well known in the art may be used in the present invention. In particular, cell adhesion promoters can be selected from collagen, gelatin, glucosaminoglycans, fibronectins, lectins, polycations (such polylysine, chitosan and the like), extracellular matrix, degradation products of cells or tissues, or any other natural or synthetic biological cell adhesion agent.

Cell adhesion promoters or marking agents are introduced on microspheres by chemical coupling procedures well known in affinity chromatography, referred to by the term "ligand immobilization". Another method of introduction is by diffusion within the gel network that constitutes the bead and then trapping the diffused molecules in place by precipitation or chemical cross-linking. Therapeutic agents, drugs or any other active molecules that are suitable for transportation by the beads can also be introduced into the microspheres prior to injection.

The microspheres of the present invention also can be chemically modified so that they will "carry" therapeutic effects, vascularization effects, anti-vascularization effects, visualization properties, anti-inflammatory, anti-bacterial, (antibiotic), anti-histamine, or combinations thereof. The chemical modification of the microspheres of the present invention is made possible by the fact that the microspheres comprise particles made of polymers that are crosslinked so that they can contain chemicals within their structures that possess various properties and that they possess unique characteristics associated with surface covalent bonds.

Incorporation of active molecules, such as drugs, into the microspheres of the present invention can be accomplished by mixing dry microspheres with solutions of said active molecules or drugs in an aqueous or hydro-organic solution. The microspheres swell by adsorbing the solutions and incorporate the active molecule of interest into the microparticle network. The active molecules will remain inside the microsphere due to an active mechanism of adsorption essentially based on ion exchange effect. The microparticles by their nature carry cationic groups and have the ability to adsorb anionic molecules, such as well known anti-inflammatory drugs, and these anionic molecules are then released slowly upon injection into the patient due to the action of physiological salt and pH. The ability of various types of microspheres to adsorb drug molecules may be readily determined by the skilled artisan, and is dependent on the amount of cationic monomers present in the initial solution from which the microspheres are prepared.

Microspheres of the present invention further possess the property of non-aggregating, which usually results from an ionic charge of the microspheres. This allows easier injection and more effective dermal augmentation, especially in situations where cells are associated with the microspheres. This property is important to dermal augmentation of the present invention because it makes injection of the microspheres through 30 gauge or smaller needles possible and easier. This property of the microspheres also prevents them from aggregating or adhering to syringe or needle walls or other device used in the process.

The microspheres of the invention can be obtained by standard methods of polymerization described in the art such as French Patent 2,378,808 and U.S. Pat. Nos. 5,648,100 and 5,635,215 each of which is incorporated herein by reference. In general, the polymerization of monomers in solution is carried out at a temperature ranging between about 0° C. and about 100° C. and between about 40° C. and about 60° C., in the presence of a polymerization reaction initiator.

Microspheres of the present invention can also be prepared by suspension polymerization, drop-by-drop polymerization or any other method known to the skilled artisan. The mode of microsphere preparation selected will usually depend upon the desired characteristics, such as microsphere diameter and chemical composition, for the resulting microspheres. The microspheres of the present invention can further be made by methods of polymerization described in the art (see, e.g., E. Boschetti, *Microspheres for Biochromatography and Biomedical Applications. Part I, Preparation of Microbeads* In: *Microspheres, Microencapsulation and Liposomes*, John Wiley & Sons, Arshady R., Ed., 2:171–189 (1999), which is incorporated herein by reference). Microspheres can also be prepared starting from an aqueous solution of monomers containing adhesion agents such as collagen (gelatin is a denatured collagen). The solution is then mixed with a non-aqueous-compatible solvent to create a suspension of droplets, which are then turned into solid gel by polymerization of monomers by means of appropriate catalysts. Microspheres are then collected by filtration or centrifugation and washed.

4.2 Injectable Composition

The present invention provides an injectable composition suitable for dermal augmentation. Specifically, the suspension comprises biocompatible, swellable, hydrophilic, non-toxic, and substantially spherical microspheres and a biocompatible carrier. The composition is injectable through needles of about 30 gauge or smaller and said microspheres are not capable of being digested or eliminated by macrophage or other elements of said mammal's immune system.

The various specific and preferred embodiments for microspheres described in §4.1 can be used in the injectable composition.

The injectable suspension of the present invention preferably comprises cells. The cells are preferably associated with the microspheres. More preferably, the cells are autologous cells from the subject mammal. These autologous cells are preferably the same type of cells that need to be repaired in the dermal augmentation, such as fat cells, muscle cells, subcutaneous cells, dermal cells, epidermal cells, or combinations thereof. The autologous cells may also preferably be cells that enhance or promote the growth or connection of cells or tissues, such as fibroblast.

Many types of emulsion and solvents can be used as the biocompatible carrier for the injectable composition. The solvent is preferably in such a condition that the microspheres can be uniformly suspended and, more importantly, that the swelling of the microspheres are also controlled by adjusting the solvent, the salt and ionic concentration, the pH value, or combinations thereof. Suitable solvents for the present invention include aqueous based solutions such as saline solutions, PBS solutions, alcohol based solutions, and other biocompatible hydro-organic solutions known in the art.

Salt concentration and pH level of the solvent are useful to control the degree of swelling of the microspheres once they are suspended in the solvent. The presence of cations such as sodium, potassium, calcium, magnesium, iron, zinc, and ammonium has various level of effects on the degree of swelling of the microspheres depending on the specific polymer and salt used. The degree of swelling of the microspheres is partially controllable by changing the balance of smaller cations and larger cations between the solvent and the microspheres. In a preferred embodiment, the contrasting agent associated with the microspheres serves as an agent controlling the degree of swelling of the microspheres. A salt level of 0.01 M to 5 M is effective to keep the microspheres from swelling. While the microspheres swell uninhibitedly under a neutral pH level, the change of pH level will affect the degree of swelling. For the anionic microspheres, the preferred pH level to shrink the microspheres or to keep them from swelling is from about 0.1 to 5. For the cationic microspheres, a pH level ranges from about 6 to about 11 will shrink the microspheres or keep them from swelling.

Upon suspension in the solvent and before injection, the microspheres may swell and the degree of swelling is controlled by the solvent and other conditions, such as time and temperature of suspension. The pre-injection swelling of the microspheres is further determined by the desired after-injection-swelling for the microspheres. Thus, microspheres that have obtained high degree of swelling before injection will swell little after injection, whereas microspheres that have swelled little before injection will obtain a higher degree of swelling after injection. The size of the microspheres before, during and after injection is always controlled such that they are easily injectable through 30 gauge or smaller needles yet become secured at the site of injection.

The biocompatible carrier of the present invention can also be an emulsion. In this embodiment, the properties of the microspheres, especially their size and degree of swelling, are preserved through the well controlled balance between the aqueous and the non-aqueous phases in the emulsion.

Preferably, the injectable composition of the present invention comprise the microspheres in an amount from about 10% to about 90% by weight and the biocompatible carrier in an amount from about 10% to about 90% by weight. More preferably, the amount ranges from 10% to 50% by weight for microspheres and from 50% to 90% for biocompatible carrier. The relative amount of the microspheres and the carrier changes according to the need of the specific dermal augmentation performed, depending on factors such as size of needle used, type of microspheres and carriers used, type of skin deficiency, area of injection, type of tissue or cells being augmented, and whether cells are associated with the microspheres prior to injection.

To prepare a suspension of the microspheres, dried sterilized microspheres are mixed with the desired solvent at a predetermined time such that the pre-injection swelling of the microspheres is controlled. The solvent can be pre-sterilized or the suspension of microspheres and the solvent can be sterilized together before injection thereof. Factors such as the material, size and crosslinking degree of the microspheres; the type, volume, salt concentration, pH level and temperature of the solvent; and the time of mixing are all considered before an injectable suspension is made and the injection is carried out thereafter.

The composition of the present invention is easily injectable, through needles of 30 gauge or smaller, into all parts of the mammal in need of treatment without causing significant pain or discomfort. This is due to, among other factors, the size and the physical resiliency of the microspheres, the biocompatible nature of the carrier, and the amount of the composition administered in accordance with the character and location of the skin deficiency.

4.3 Method of Dermal Augmentation

The present invention further provides methods of causing dermal augmentation and treating skin deficiencies. The methods comprise injecting a suspension of biocompatible, swellable, hydrophilic, non-toxic and substantially spherical microspheres in a biocompatible solution to a mammal. The method further specifies that the suspension is injectable through a needle of about 30 gauge or smaller and the microspheres are not capable of being digested or eliminated by macrophage or other elements of the mammal's immune system.

The various specific and preferred embodiments of the microspheres and the injectable suspension described in §4.1 and §4.2 can be used in the method for dermal augmentation.

The injection can be carried out by syringe, catheters, needles and other means for injecting or infusing microspheres in a liquid medium. In a preferred embodiment of the present invention, the injection of the injectable composition to the subject mammal is carried out by injecting the composition into an area of the mammal in need of dermal augmentation through a needle of 30 gauge or smaller. The injection can be performed on any area of the mammal's body that is in need of treatment, including, but not limited to, face, neck, torso, arms, hands, legs, and feet. The injection can be into any position in the specific area such as epidermis, dermis, fat, or subcutaneous layer. A particular effective position of injection according the present invention's methods, is the subcutaneous layer, which allows the microspheres and the associated agents and cells perform more effectively. In a preferred embodiment of the present invention, the mammal is a human.

The frequency and the amount of injection under the present invention is determined based on the nature and location of the particular skin deficiency being treated. Generally, because of the stable and long lasting character of the present invention's injectable composition, multiple injections are not necessary. In certain cases, however, repeated injection may be necessary to achieve optimal results. A skilled practitioner should be able to determine the frequency and the amount of the injection for each particular case.

According to the present invention's methods, after injection, microspheres become secured at the position of the injection. The microspheres are not digested or eliminated by macrophage or other elements of the immune system. Furthermore, the microspheres will not displace or slide away from the position of injection. The secure of the microspheres at the position of injection is due to, among other factors, their size, physical resiliency, and hydrophilicity. The swellability of the microspheres at the site of injection is important in helping secure the microspheres at the site of injection. Upon contacting the physiological fluids and the cells at the site of injection, the microspheres may further swell if there is no pre-injection swelling or the swelling is controlled to a lower level. The physiological condition, including salt concentration (e.g., sodium and potassium) and pH level, may further help the microspheres swell to the desired size.

This property of the microspheres allows precise control of the injection and makes it possible that the microspheres work together at position of injection and provide a scaffold for effective dermal augmentation. In fact, the present invention has discovered that, because of the precision of the injection and the securing of the microspheres at the site of injection provided by the invention, it is now possible to create a scaffold of microspheres at the site of injection without forming a scaffold of the microspheres before injection. The "injectable scaffold" of the present invention is especially advantageous over prior art in which surgical procedures are necessary in order to implant a scaffold for certain dermal augmentation. This discovery significantly reduces the complexity of dermal augmentation when a scaffold is desired for more effective dermal augmentation in certain cases. This unique contribution of the present invention to dermal augmentation and the treatment of skin deficiencies is made possible, in part, by the well controlled size and degree of swelling of the microspheres, as discussed above. The ability of forming a scaffold at the injection site without forming a scaffold before the injection makes the microspheres of the present invention particularly effective in providing dermal augmentation. The size of the scaffold is determined by the amount and frequency of the injection, which is in turn determined by the nature and location of the skin deficiency being treated. A skilled practitioner would appreciate the teaching of the present invention as a whole and be able to determine the exact amount and frequency of injection for each particular case.

According to the present invention, the method for causing dermal augmentation is particularly suitable for treatment of skin contour deficiencies, which are usually results of aging, environmental exposure, weight loss, child bearing, injury, surgery, or combinations thereof. Aging and environmental exposure often cause wrinkles on various positions of the skin. Weight loss and child bearing, on the other hand, often cause stretch marks on various positions of the skin, especially on stomach, areas of the lower body, and legs. Injury and surgery often result in scars in areas of injury and operation. Specific contour deficiencies suitable for treatment by the present invention's method include, but not limited to, frown lines, worry lines, wrinkles, crow's feet, marionette lines, stretch marks, and internal and external scars including scars resulted from injury, wounds, accidents, bites, surgery. The method of the present invention advantageously provides dermal augmentation treatment for these various contour deficiencies in an effective, longer lasting, and stable manner. Particularly suitable for treatment according to the present invention are contour deficiencies of such areas as eyes, cheeks, nose, lips, forehead, and neck.

The present invention also provides method for treating skin deficiencies, especially deficiencies caused by diseases such as acne and cancer. These deficiencies can be direct or indirect results of the diseases, such as deficiencies caused by the treatment of the diseases.

The present invention further provides method of causing dermal augmentation by injecting the injectable composition not directly into the body, but extracorporeally into organs, components of organs, or tissues prior to the inclusion of said tissues, organs or components of organs into the body.

The injection method of the present invention can be carried out by any type of sterile needles of 30 gauge or smaller and corresponding syringes or other means for injection, such as a three-way syringe. The needles, syringes and other means for injection are commercially available from suppliers such as VWR Scientific Products (West Chester, Pa.), Beckton Dickinson, Kendal, and Baxter Healthcare. The size of the syringe and the length of the needle used will dependent on the particular injection based on factors such as the specific disease or disorders being treated, the location and depth of the injection, and the volume and specific composition of the injectable suspension being used. A skilled practitioner will be able to make the selection of syringe and needle based on experience and the teaching of the present invention.

The present invention additionally provides a kit for performing dermal augmentation. The kit comprises a 30 gauge or smaller needle and a corresponding syringe, wherein the syringe optionally contains a composition comprising biocompatible, swellable, hydrophilic, non-toxic and substantially spherical microspheres and a biocompatible carrier. The composition is injectable through the needle and the microspheres are not capable of being digested or eliminated by macrophage or other elements of said mammal's immune system. Alternatively, the dermal augmentation kit comprises a 30 gauge or smaller needle, a corresponding syringe, and separate containers containing the microspheres in dried form and the biocompatible solvent. The dried sterilized microspheres and the solvent are ready to be mixed for injection either in their respective containers or in the syringe. These dermal augmentation kits are sterile and ready to use. The kits are designed in various forms based the sizes of the syringe and the needles and the volume of the injectable composition contained therein, which in turn are based on the specific skin deficiencies the kits are designed to treat.

The invention is further defined by reference to the following examples that describe in detail the preparation of microspheres, the preparation of injectable composition, and the method of causing dermal augmentation using the injectable composition. The following examples are illustrative only and should in no way limit the scope of the present invention. It will be apparent to those skilled in the art that many modifications, both to materials and methods, may be practiced without departing from the purpose and scope of this invention.

5. EXAMPLES

Example 1

In a beaker containing 100 ml of demineralized water, 58 g of sodium chloride and 27 g of sodium acetate are dissolved. One adds 400 ml of glycerol and then the pH is adjusted between 5.9 and 6.1. Then 90 g of N-tris-hydroxymethyl methylacrylamide, 35 mg of diethylaminoethylacrylamide and 10 g of N,N-methylene-bis-acrylamide are added. One heats at 60–70 C. and 100 mo of a hot 300 mg/ml gelatin solution is added. The total volume of the mixture is adjusted to 980 ml by addition of hot water and then 20 ml of a 70 mg/ml ammonium persulfate solution and 4 ml of N,N,N',N'-tetramethylethylenediamine are added.

This solution is poured into paraffin oil at 50–70 C. stirring. After a few minutes, the polymerization reaction of acrylic monomers is manifested by an increase of temperature. The microspheres are then recovered by decanting, washed carefully, screened and sterilized in an autoclave in a buffered medium.

Those microspheres, after screen calibration, possess the characteristics desired for dermal augmentation, including a marked cationic charge and an effective adhesion agent (gelatin or denatured collagen).

Example 2

The procedure of Example 1 is followed, using triethylaminoethyl acrylamide instead of diethylaminoethyl acrylamide. After recovery or the spheres, the gelatin is reticulated by means of a 25% glutaraldehyde solution (100 ml of all of the microspheres). The treatment is carried out stirring at 4 C. overnight. It is followed by a washing with demineralized water.

Examples 3 and 4

The procedure of Examples 1 and 2 is followed, replacing 10 g of N-tris-hydroxymethyl methylacrylamide with 10 g of acrylic acid. The microspheres obtained possess high swellability that is controllable by salt and ionic concentration and pH level. Those microspheres are advantageously usable in direct view of the user at the time of handling.

Examples 5 and 6

The procedure of Examples 1 and 2 is followed, replacing N-tris-hydroxymethyl methylacrylamide with 10 g of N-acryloyl hexamethylene Procion Red HE-3B. The microspheres obtained possess an intense red coloration due to the integration of the acrylic dye in the polymer lattice. Those microspheres are advantageously usable in direct view of the user at the time of handling.

Examples 7 and 8

One hundred milliliters of microspheres obtained according to Examples 1 to 4 are washed with a 0.1 M borate buffer of pH 8 and then suspended in 50 ml of a 5 mg/ml rhodamine isothiocyanate solution. The suspension is then stirred for at least 15 hours, after which it is washed with a neutral buffer to a colorless supernatant.

Those fluorescent red-colored microspheres are then calibrated and sterilized, and can be used in dermal augmentation.

Examples 9 and 10

The procedure of Examples 1 to 4 is followed, replacing 10 g of N-tris-hydroxymethyl methylacrylamide with 10 g of a monomer opaque to X-rays, (acrylamido-3-propionamido)-3-triiodo-2,4,6-benzoic acid.

The microspheres obtained possess the property of absorbing X-rays and are therefore of particular interest in their in vivo follow-up after dermal augmentation.

Examples 11 to 14

The procedure of Examples 1 to 2 is followed, adding to the initial monomer solution 5 g of a radio-opaque soluble linear polymer, acrylamino-3-triiodo-2,4,6-benzoic polyacid (Examples 11 and 12) or (acrylamino-3-propionamido)-3-triiodo-2,4,6-benzoic polyacid (Examples 13 and 14).

Those polymers, having a molecular weight exceeding 100,000 Dalton, are imprisoned in the polymer lattice and, without disturbing the general properties of the microspheres for the applications claimed, make it possible to attain a radiopacity usable for the in vivo follow-up of dermal augmentation procedure.

Examples 15 and 16

The procedure of Examples 1 and 2 is followed, adding to the initial monomer solution 200 g of barium sulfate power. The microspheres obtained are opaque to both visible light and X-rays.

Examples 17 and 18

The procedure of Examples 1 and 2 is followed, adding 50 mg of magnetite (Fe3O4) to the initial monomer solution.

The microspheres obtained have the property of being detected in (Magnetic Resonance Imaging) MRI imagery.

Example 19

Comparative Evaluation of Two Types of Nonresorbable Spheres

The study consisted of injecting two types of calibrated microspheres, some prepared according to Example 2, the others of polystyrene (Biosilon Nunc Danemark), in pulmonary arterial vascularization of the rat and of observing on days 0, 8 and 30 the extent of the cell reaction and the remodeling modalities of the occluded vessels.

The study revealed four important facts:

placement in suspension and vascular injection of the polystyrene spheres is difficult and clusters are formed at the segmental narrowing constituting the nozzle of the syringe, the base of the catheter and the possible changes of diameter of the catheters;

the cell reaction is earlier, more intense and more durable with the spheres of Example 1 than with polystyrene. On the 8th day the thickness of the cell reaction covering the spheres of the invention is almost three times greater than that covering the polystyrene spheres (34 µm as compared to 13 µm);

there is no differences in kinetics in the vascular remodeling with either material;

no phenomenon suggesting the toxicity of either material was observed.

In conclusion, the microspheres of the invention are more manageable and more effective as adhesive agent.

Example 20

Preparation of Injectable Suspension

A suspension of 40 µm to 120 µm polyacrylamide copolymer microspheres in an oily contrast medium is prepared.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference. Other embodiments are within the following claims.

What is claimed is:

1. An injectable composition suitable for dermal augmentation in a mammal which comprises biocompatible, swellable, hydrophilic, non-toxic and substantially spherical microspheres and a biocompatible carrier, wherein said composition is injectable through needles of about 30 gauge or smaller and wherein said microspheres swell to a predetermined size after injection wherein the biocompatible carrier comprises salts composed of cations selected from the group consisting of sodium, potassium, calcium, magnesium, iron, zinc, and ammonium in an amount of from about 0.01 M to about 5 M, and wherein the composition comprises the microspheres in an amount from about 10% to about 50% by weight and the biocompatible carrier in an amount from about 50% to about 90% by weight.

2. The composition of claim 1, wherein the composition is a suspension of said microspheres in said biocompatible carrier.

3. The composition of claim 2, wherein the biocompatible carrier is an emulsion.

4. The composition of claim 2, wherein the biocompatible carrier is an organic or non-aqueous solution.

5. The composition of claim 2, wherein the biocompatible carrier is an aqueous based solution, a hydro-organic solution, or mixtures thereof.

6. The composition of claim 1, wherein the salt is supplied in form of a contrast agent.

7. The composition of claim 2, wherein the biocompatible carrier is acylamino-e-propion-amido-3-triiodo-2,4,6-benzoic acid.

8. The composition of claim 1, wherein there is no aggregation or clumping of the microspheres prior to and during injection.

9. The composition of claim 1, wherein the microspheres comprise sodium acrylate polymer, acrylamide polymer, acrylamide derivative polymer or copolymer, sodium acrylate and vinyl alcohol copolymer, vinyl acetate and acrylic acid ester copolymer, vinyl acetate and methyl maleate copolymer, isobutylene-maleic anhydride crosslinked copolymer, starch-acrylonitrile graft copolymer, crosslinked sodium polyacrylate polymer, crosslinked polyethylene oxide, or mixtures thereof.

10. The composition of claim 9, wherein the polymers comprise from about 0.5% to about 20%, by molecular weight, of crosslinkers.

11. The composition of claim 1, which further comprises cells associated with surfaces of at least a portion of the microspheres prior to injection.

12. The composition of claim 11, wherein the cells are autologous cells from the subject mammal.

13. The composition of claim 12, wherein the autologous cells are fat cells, muscle cells, subcutaneous cells, dermal cells, epidermal cells, or combinations thereof.

14. The composition of claim 1, further comprises therapeutic agent, radio-pacifying agent, contrast medium, or mixtures thereof.

15. The composition of claim 14, wherein said agents or medium are bound to the microspheres.

16. The composition of claim 14, wherein the therapeutic agent is anti-inflammatory agent.

17. The composition of claim 1, wherein the microspheres are capable of being chemically modified to have therapeutic effects, anti-inflammatory effects, anti-bacterial effects, antihistamine effects, or combinations thereof.

18. A method of dermal augmentation in a mammal comprising injecting a composition comprising biocompatible, swellable, hydrophilic, non-toxic and substantially spherical microspheres in a biocompatible carrier to said mammal through a needle of about 30 gauge or smaller wherein the biocompatible carrier comprises salts composed of cations selected from the group consisting of sodium, potassium, calcium, magnesium, iron, zinc, and ammonium in an amount of from about 0.01 M to about 5 M, and wherein the composition comprises the microspheres in an amount from about 10% to about 50% by weight and the biocompatible carrier in an amount from about 50% to about 90% by weight.

19. The method of claim 18, wherein the composition is a suspension of said microspheres in said biocompatible carrier.

20. The method of claim 18, wherein the microspheres comprise sodium acrylate polymer, acrylamide polymer, acrylamide derivative polymer or copolymer, sodium acrylate and vinyl alcohol copolymer, vinyl acetate and acrylic acid ester copolymer, vinyl acetate and methyl maleate copolymer, isobutylene-maleic anhydride crosslinked copolymer, starch-acrylonitrile graft copolymer, crosslinked sodium polyacrylate polymer, crosslinked polyethylene oxide, or mixtures thereof.

21. The method of claim 18, which further comprises cells associated with surfaces of at least a portion of the microspheres prior to administration.

22. The method of claim 21, wherein the cells are autologous cells from the subject mammal.

23. The method of claim 22, wherein the autologous cells are fat cells, muscle cells, subcutaneous cells, dermal cells, epidermal cells, or combinations thereof.

24. The method of claim 19, wherein the biocompatible carrier is an emulsion.

25. The method of claim 19, wherein the biocompatible carrier is organic or non-aqueous solvent.

26. The method of claim 19, wherein the biocompatible carrier is an aqueous solution, a hydro-organic solution, or mixtures thereof.

27. The method of claim 19, wherein the salt is supplied in form of a contrast agent.

28. The method of claim 19, wherein biocompatible solvent is acylamino-e-propion-amido-3-triiodo-2,4,6-benzoic acid.

29. The method of claim 18, wherein the composition further comprises therapeutic agent, radio-pacifying agent, contrast media, or mixtures thereof.

30. The method of claim 29, wherein said therapeutic agents are bound to the microspheres.

31. The method of claim 18, wherein the microspheres are capable of being chemically modified to have therapeutic effects, anti-inflammatory effects, anti-bacterial effects, antihistamine effects, or combinations thereof.

32. The method of claim 31, wherein the chemical modification of the microspheres are caused by interactions between the microspheres and neighboring tissues after injection thereof.

33. The method of claim 18, wherein the injection is into an area of said mammal in need of dermal augmentation.

34. The method of claim 33, wherein the administration comprises injecting said composition into the subcutaneous layer.

35. The method of claim 18, wherein the dermal augmentation is for treatment of contour deficiencies of said mammal.

36. The method of claim 35, wherein the contour deficiencies are caused by aging, environmental exposure, weight loss, child bearing, surgery, disease or combinations thereof.

37. The method of claim 35, wherein the contour deficiencies are one or more of the group consisting of frown lines, worry lines, wrinkles, crow's feet, marionette lines, stretch marks, and internal and external scars resulted from injury, wound, bite, or surgery.

38. The method of claim 36, wherein the disease is acne, cancer, or combination thereof.

39. The method of claim 18, wherein the mammal is human.

40. The method of claim 18, wherein the administration comprises injecting said composition extracorporeally into organs, components of organs, or tissues prior to their inclusion into said mammal's body, organs, or components of organs.

41. A kit for performing dermal augmentation comprising:
   (a) a 30 gauge or smaller needle;
   (b) means for injecting a liquid based composition through said needle; and
   (c) biocompatible, swellable, crosslinked, hydrophilic, non-toxic and substantially spherical microspheres and a liquid based biocompatible carrier injectable through said needle and are not capable of being digested or eliminated by macrophage or other elements of said mammal's immune system after injection thereof wherein the biocompatible carrier comprises salts composed of cations selected from the group consisting of sodium, potassium, calcium, magnesium, iron, zinc, and ammonium in an amount of from about 0.01 M to about 5 M, and wherein the composition comprises the microspheres in an amount from about 10% to about 50% by weight and the biocompatible carrier in an amount from about 50% to about 90% by weight.

42. The kit of claim 41, wherein the means for injection is a syringe corresponding to said needle.

43. The kit of claim 41, wherein the microspheres are suspended in the biocompatible carrier.

44. The kit of claim 43, wherein the microspheres are associated with cells.

* * * * *